United States Patent [19]

Swank

[11] 4,115,277
[45] Sep. 19, 1978

[54] BLOOD FILTERING APPARATUS OF GRADUATED FIBER DENSITY

[75] Inventor: Roy L. Swank, Portland, Oreg.

[73] Assignee: Pioneer Filters, Inc., Beaverton, Oreg.

[21] Appl. No.: 807,378

[22] Filed: Jun. 17, 1977

[51] Int. Cl.² ............................................. B01D 23/20
[52] U.S. Cl. .................................. 210/436; 210/489; 210/496; 210/DIG. 23
[58] Field of Search ............... 210/232, 436, 455, 483, 210/489, 496, DIG. 23

[56] References Cited

U.S. PATENT DOCUMENTS

| | | | |
|---|---|---|---|
| 837,845 | 12/1906 | Kiefer | 210/455 |
| 2,692,654 | 10/1954 | Pryor | 210/489 X |
| 3,069,831 | 12/1962 | Young et al. | 210/496 X |
| 3,111,489 | 11/1963 | Getzin | 210/232 |
| 3,593,854 | 7/1971 | Swank | 210/436 |
| 3,935,111 | 1/1976 | Bentley | 210/489 X |

Primary Examiner—Frank A. Spear, Jr.
Assistant Examiner—Richard W. Burks
Attorney, Agent, or Firm—Eugene D. Farley

[57] ABSTRACT

A filter for filtering blood during surgery or dialysis by passing it through a fibrous filter mat for removal of blood cell aggregates and extraneous particulate debris, and for separation of entrained air. The presenting surface of the filter mat comprises a plurality of fluffed regions, each of graded fiber density, for selective filtration of blood aggregates and debris.

8 Claims, 5 Drawing Figures

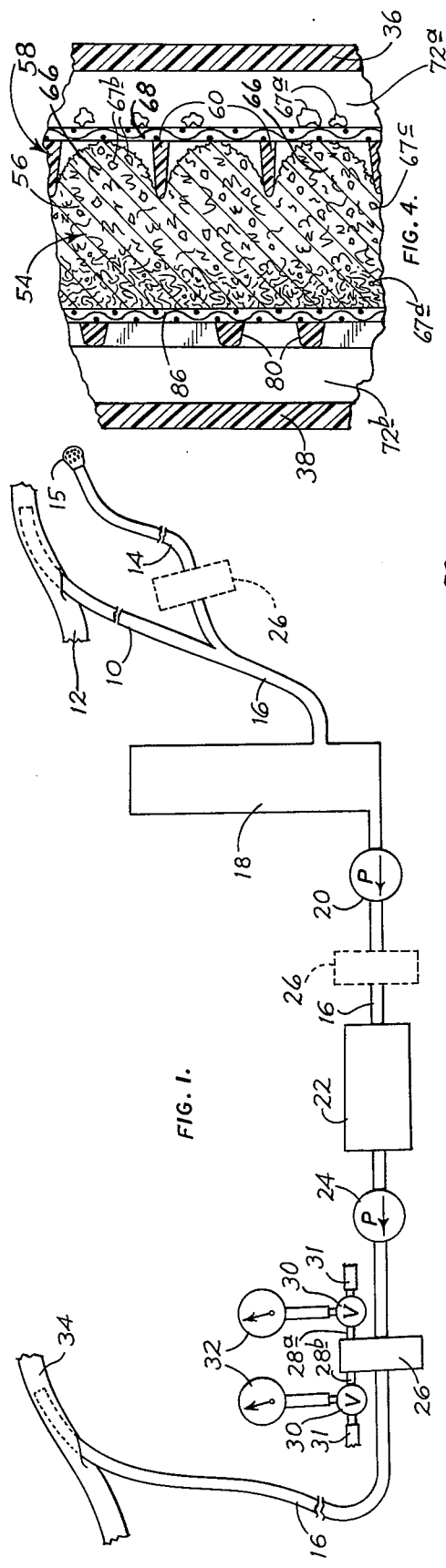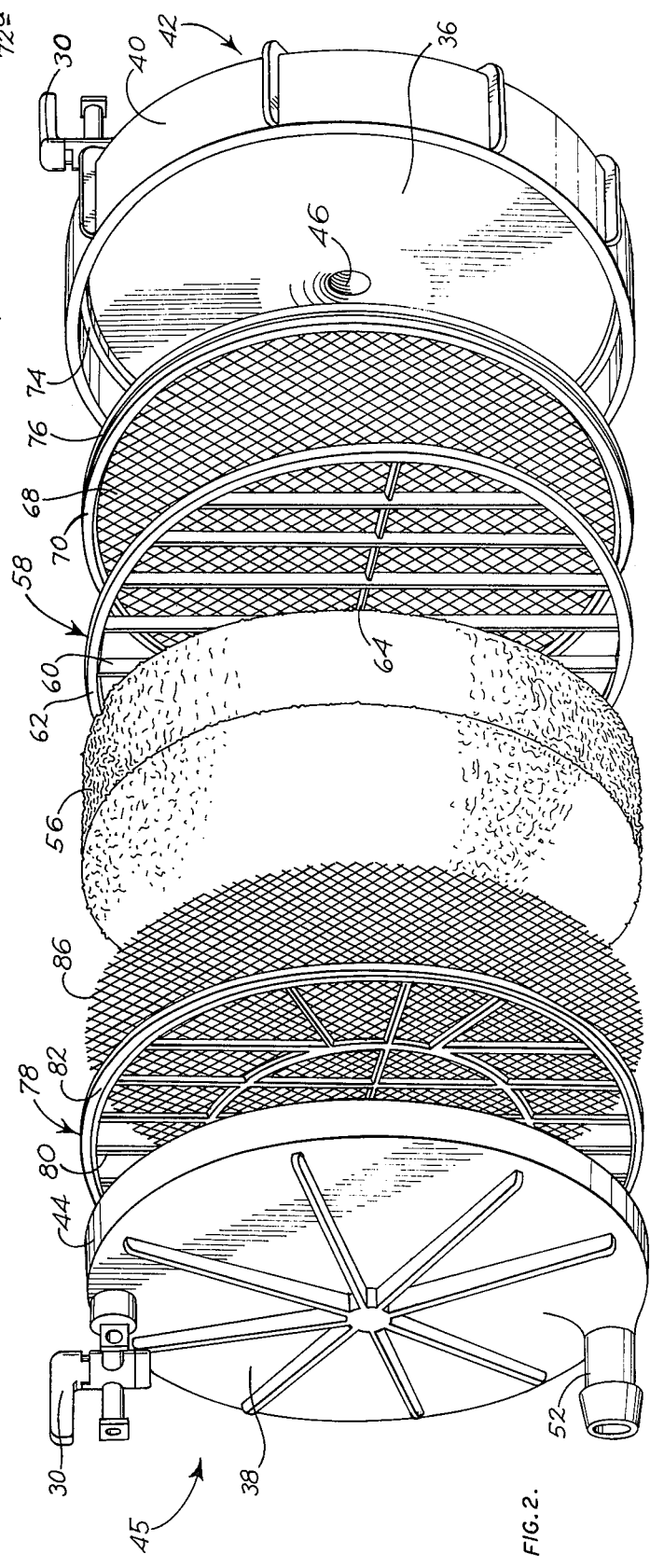

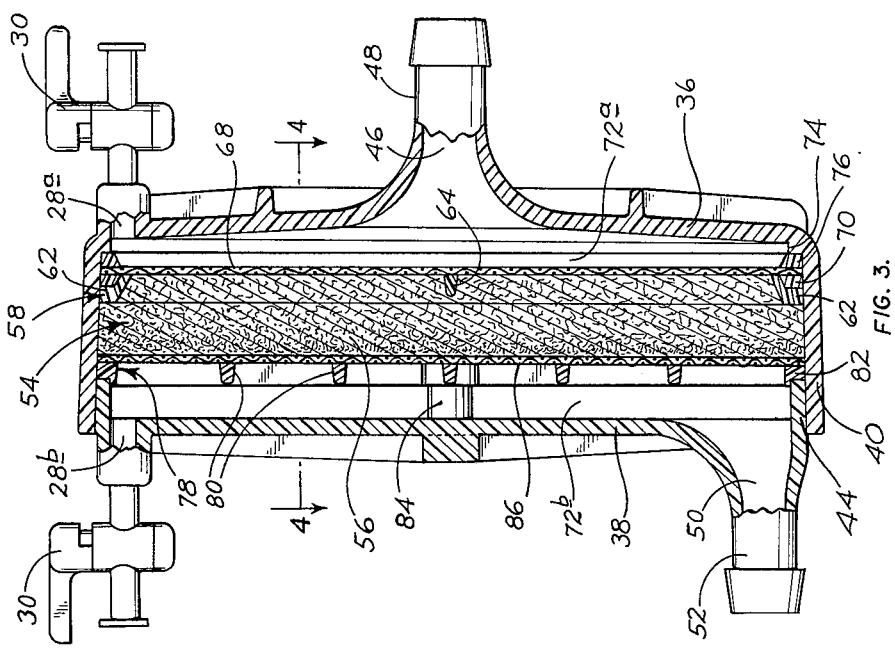
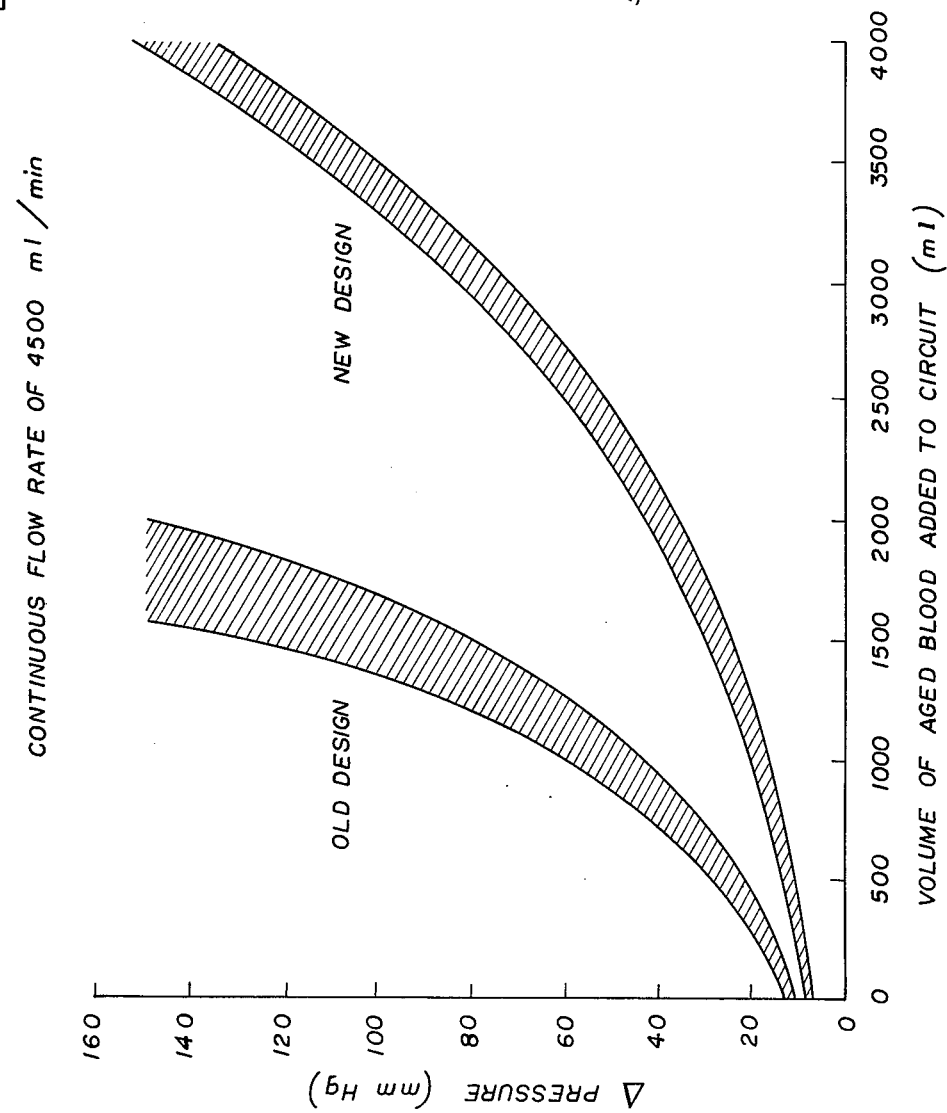
FIG. 3.
FIG. 5.

BLOOD FILTERING APPARATUS OF GRADUATED FIBER DENSITY

BACKGROUND AND SUMMARY OF THE INVENTION

The present invention relates to blood filters and particularly to continuous, high-volume blood filtering devices suitable for handling blood during heart surgery, kidney dialysis, etc.

In blood transfusions and heart surgery, it has become routine to employ blood bank blood. This is prepared by withdrawing blood from donors, adding heparin or other anti-coagulants, and then storing the blood under carefully controlled conditions until its use is required.

Whether it is used directly in transfusions or in heart surgery, there sometimes have been observed in the patient an ensuing cessation of circulation and other reactions not attributable to mismatching of blood types. Although the cause of this regrettable result is not known, it is recognized as a function of blood storage duration. Accordingly, it is common practice to discard blood bank blood after it has been stored for a predetermined time.

Another difficult problem exists when handling blood during heart surgery, kidney dialysis, etc. In these procedures not only is the blood altered to produce harmful constituents, but it becomes contaminated with extraneous material such as epithelium, pieces of muscle, fat emboli, fragments of suture material and entrained air. This foreign material must be removed in order successfully to consummate the surgical procedure.

In my patent application entitled "Blood Treating and Filtering Apparatus", Ser. No. 882,663, filed Dec. 5, 1969, now U.S. Pat. No. 3,593,854, I describe a blood filtering unit for removing blood debris, harmful constituents, and entrained air from blood at a high-volume rate suitable for use in open heart surgery. This apparatus has proved effective and reliable in the surgical setting for which it was designed. However, continued surgical experience with the unit has shown that the fibrous filter mat used in the unit tends to become clogged at its upstream, or presenting, surface before the filtering capacity of the filter pad is reached, thereby shortening the life of the filtering unit, and adding expense and inconvenience to the blood filtering operation.

The causes of filter surface clogging can be appreciated from the following brief description of the surgical blood filtering unit disclosed in the above-cited U.S. Pat. No. 3,593,854. This filtering unit comprises a flow chamber and a fibrous filter mat laterally supported within the chamber by upstream and downstream perforated discs. In the assembled unit, the perforated discs are coextensive with, and firmly abut, the upstream and downstream surfaces of the filter mat, exposing at the disc perforations a plurality of small flat surface regions having uniform fiber density. In particular, the fiber density at the presenting surface regions is essentially the same as the fiber density throughout the filter mat. Because the filter mat density must be sufficient to filter small cellular debris in the blood, the presenting surface regions of the filter mat must be necessarily filter such small debris also. As a result, blood debris tends to stack upon the filter pad surface, and this, coupled with the limited area of the presenting surface regions, leads to premature clogging.

The present invention overcomes the above-described problem of clogging at the filtering surface. In the apparatus of my new design, the filter mat is supported upstream by a grill having a plurality of substantially deep ribs for indenting the upstream surface of the mat, thereby forming a plurality of fluffed surface regions, each of graded fiber density, in the interrib spaces. The fluffed surface regions serve both to increase the presenting area of the filter mat and, more importantly, to permit size-selection filtration of blood debris at the filter pad surface. Experimentally, the filtering unit of the new design has a capacity for blood cell aggregates approximately two to three times that of the old design filtering unit described in U.S. Pat. No. 3,593,854.

It is therefore a specific object of the present invention to provide a blood filtering apparatus which overcomes the problem of surface clogging associated with the above-described old design filtering apparatus, and thus to provide a high capacity blood filter suitable for use in open heart surgery.

In the drawings:

FIG. 1 is a schematic view illustrating the application of the present invention as used in heart surgery;

FIG. 2 is an exploded view of the herein-described apparatus;

FIG. 3 is a sectional view of the same apparatus, taken along the top-to-bottom midline of the apparatus.

FIG. 4 is a fragmentary sectional view of the same apparatus taken along line 4—4 of FIG. 3; and FIG. 5 is a smooth curve plot of the pressure differential across the filtering unit as a function of the volume of old blood filtered by the filtering units of the old and new design.

Referring now to the drawings, there is shown in FIG. 1 the arrangement of various units, including the present filtering apparatus, useful for filtering blood and removing entrained air during open heart surgery.

A conduit 10 may be tied to the superior or inferior vena cava 12 using known techniques. A branch conduit 14 having a suction tip 15 made of stainless steel or other inert material is placed in the chest cavity for removal of accumulated blood.

Conduits 10 and 14 merge to form main conduit 16 which transfers blood to a reservoir 18 of suitable capacity.

The blood then passes through a first pump 20, an oxygenator 22 and a second pump 24. The latter discharges it into the herein-described blood filtering apparatus 26. It should be noted, however, that this apparatus may be located variously in the system to meet the needs of the various situations. Typical alternate locations are illustrated in dotted outline.

Air entrained in the blood is removed at the upstream and downstream sides of the filter apparatus 26 through exhaust ports 28a and 28b fitted with valves 30. Each exhaust valve port may alternatively be switched to a position communicating with an exhaust line 31, a pressure gauge 32, or to a closed position. The oxygented, treated and filtered blood then continues through the conduit the discharge end of which is tied into the femoral or other artery 34.

The construction and manner of assembly of the blood filtering unit is shown in detail in FIGS. 2, 3 and 4.

The filtering unit comprises upstream and downstream end pieces 36 and 38 and tubular body 40. The upstream end piece 36 and tubular body 40 are formed from a single molded plastic piece 42, and sealed by conventional means at the inner tubular wall to the flanged rim 44 of the downstream end piece 38, which is also formed from a single molded plastic piece 45.

The upstream end piece 36 is provided with a central inlet port 46 with outwardly-projecting nipple 48 for attachment of one segment of conduit 16. The downstream end piece 38 is provided with a discharge port 50 communicating with a nipple 52 designed to receive another segment of conduit 16.

The end pieces 36 and 38 and the tubular body 40 provide a central chamber 54 arranged for horizontal flow of blood through a disc-shaped filter mat 56 supported within the tubular body region of the chamber.

Filter mat 56 serves to remove blood cell aggregates, altered leukocytes and platelets, and particulate surgical debris from the blood. The requirements and characteristics of the filter material used in this application are detailed in the above-cited U.S. Pat. No. 3,593,854. Preferably the mat fibers are at least 100 microns in length and less than 30 microns in diameter. Typically, glass or synthetic wool fibers 2 to 4 centimeters in length and approximately 17 microns in diameter are used. The fiber density of the mat is within the range 0.1 grams per cc. to 0.4 grams per cc. At densities less than 0.1 grams per cc., efficient filtration is not obtained. At densities above 0.4 grams per cc., the filtration rate is too slow to be practical, standard filtration rates used for open heart surgery being about 4 liters per minute.

The desired fiber density gradient regions at the presenting surface of the filter mat are formed by multiply indenting the upstream filter mat surface, as shown in FIG. 4. The preferred indentation means is a grill 58 having a plurality of substantially deep indenting ribs 60. However, various other indenting means, for example, a plurality of rib or finger projections supported at the inner face of the upstream end piece 36, may alternatively be employed. The indenting means additionally serves to support the filter mat upstream in the path of blood flow.

Grill 58 is formed from a single molded plastic piece and comprises in addition to parallel indenting ribs 60 a rim 62, and a cross piece 64 substantially perpendicular to the indenting ribs which joins the center regions of the indenting ribs 60 to the rim 62 for structural support. The spacing between the indenting ribs is dictated partly by the lengths of fibers used in the filter mat. Typically, an inter-rib spacing of about 1 centimeter is used with mat fibers having 2-4 centimeter lengths.

The indenting ribs 60 are substantially deep, penetrating the filter mat approximately one-third of the filter mat thickness, as seen in FIG. 4. These ribs are tapered at their downstream edges to minimize the total indented surface area. The grill 58 thus presses into the fiber mat 56, causing the filter material between the ribs to fluff out. The fluffed regions 66 are loosely packed at the center portions of the inter-rib spaces and tightly packed near the indenting ribs, thereby forming a fiber density gradient between each pair of ribs.

The fulffed regions 66 of fiber density gradient allow inflowing blood to be classified at the filter surface on the basis of debris size, as illustrated by particles 67a, 67b, 67c, and 67d. As seen in FIG. 4, the fluffed regions also provide an increased filter mat presenting area. These two features combine to minimize the problem of surface clogging associated with the surgical blood filtering unit disclosed in U.S. Pat. No. 3,593,854.

A screen 68 is located immediately upstream of the grill 58 for trapping large debris in the blood and secondarily for retaining loose fiber filter material within the inter-rib spaces. The screen may be nylon, stainless steel, or other inert material, and has a preferred grid size of about 100 pores per square centimeter. The screen is supported at its periphery by screen rim 70.

The indenting grill 58 and screen 68 are spaced apart from the upstream end wall 36 to provide an upstream recess 72a between the upstream filter mat surface and the end wall 36. The upstream recess facilitates distribution of blood over the entire filter surface and may additionally be used to separate and remove air entrained in the blood.

Various structural arrangements may be employed to space apart the upstream grill and screen and end piece. A preferred arrangement, illustrated in FIG. 3, comprises a peripheral boss 74 formed on the upstream end piece and a spacer ring 76 which combined provide a shoulder against which the screen rim 70 and the grill rim 62 bear in the final assembly.

The filter mat is supported at its downstream end by a grill 78 having a lattice 80 supported within a rim 82. The downstream grill 78 is preferably spaced apart from the downstream end piece 38 by the end piece flanged rim 44 which provides a shoulder against which the grill rim 82 bears in the final assembly, and by center boss 84 which abuts the center region of the downstream grill.

A fine mesh screen 86, supported between the downstream grill 78 and filter mat 56, serves to screen out loose filter material which otherwise might be entrained in the outflowing blood. The screen may be made of nylon, stainless steel, or other suitable material.

The downstream recess 72b, between the downstream grill 78 and end piece 38 serves the valuable function of providing a region downstream which permits further removal of air entrained in the blood. Air entrained in the blood in either the upstream or downstream recesses will bubble upwardly to the top of the reccess, there to be evacuated through ports 28a or 28b located at the top of the recesses 72a and 72b. Port valves 30 may be switched to a position communicating with exhaust tubes 31 or with pressure gauges 32, or switched to a closed position.

Thus, in application of the form of the invention illustrated in FIGS. 2, 3 and 4, blood entering through inlet port 46 spreads out over the area of the upstream recess 72a. Here the largest blood debris particles 67a are trapped against the upstream screen 68. As the blood passes through the screen 68 and enters the fiber filter mat, the blood debris is selectively filtered, the next larger particles 67b being trapped at the surface regions of lower fiber density, and the smaller particles 67c, at the surface regions of higher fiber density. The smallest particles 67d including small blood cell aggregates and altered leukocytes and platelets are removed primarily within the filter mat. This size-classifying effect is illustrated in FIG. 4.

Contemporaneously, the air entrained in the blood is separated in the two recesses 72a and 72b, bubbling to the top of these recesses where it is removed through ports 28a and 28b.

The filtering capacities of the old and new design filtering units were experimentally compared as follows:

Two liters of outdated blood, diluted to 32% hematocrit with normal saline, was extensively filtered through the present new design filtering unit to remove filterable blood debris. This filter was then replaced in the blood flow system by the test filtering unit. The filtered blood was circulated through the test unit at a rate of 4.5 liters per minute for three minutes, at the end of which time the pressure diferential across the filtering unit valves was determined from pressure gauges 32.

500 Ml. of filtered blood was then removed from the blood flow system and replaced with 500 ml. of the outdated blood diluted to 32% hematocrit, and the blood was again circulated through the test filtering unit at a rate of 4.5 liters per minute for three minutes to obtain a second pressure differential reading. This procedure was repeated for successive 500 ml. increments of outdated blood until a final pressure differential of 1500 mm. Hg. was reached, this pressure differential being above the useful operating pressure differential of the filtering unit. The pressure differentials recorded at the 500 ml. blood volume increments are plotted in smooth curve form in FIG. 5.

It is clear from this figure that the present new design filtering unit is substantially more efficient than the old design unit described in U.S. Pat. No. 3,593,854, filtering the same amount of outdated blood at lower pressure differentials. More importantly, the filtering capacity of the new design, in the range of useful operating pressure differentials, is two to three times that of the old design, providing obvious cost and convenience advantages in the surgical setting.

The present invention therefore provides a high capacity blood filtering apparatus for removing blood debris and altered blood constituents efficiently and at a high rate sufficient to accommodate the needs of open heart surgery.

Having thus described my invention in preferred embodiments, I claim as new and desire to protect by Letters Patent:

1. A high volume, continuous filter for debris-containing blood, comprising:
    (a) a blood flow chamber having a blood inlet port at one end and a blood outlet port at the opposite end,
    (b) a filter mat of fibrous material extending longitudinally in the chamber and interposed between the inlet and outlet ports, and
    (c) a plurality of laterally spaced mat-indenting members in the chamber engaging the upstream end of the mat and indenting the mat through a portion of its longitudinal thickness in the areas of said indenting members for causing the fibrous material to fluff out in the spaces between the indenting members and thereby form regions of decreasing mat density progressively outward from said indenting members.

2. The blood filter of claim 1 wherein the indenting members comprise a grill of longitudinally deep ribs supported by a peripheral rim.

3. The blood filter of claim 2 wherein the ribs are tapered to reduced thickness in the downstream direction.

4. The blood filter of claim 2 including a screen in the chamber disposed adjacent and upstream from the grill for trapping large particles of blood debris.

5. The blood filter of claim 4 including means for spacing the screen inwardly of the inlet port, forming therebetween an upstream recess for facilitating distribution of inflowing blood over the upstream surface of the mat.

6. The blood flow filter of claim 1 including support means interposed between the downstream end of the mat and the outlet port for spacing the downstream end of the mat inwardly of the outlet port.

7. A high volume, continuous filter for debris-containing blood, comprising:
    (a) a blood flow chamber having a blood inlet port at one end and a blood outlet port at the opposite end,
    (b) a filter mat of fibrous material extending longitudinally in the chamber and interposed between the inlet and outlet ports,
    (c) a grill of a plurality of longitudinally deep and laterally spaced mat indenting ribs supported by a peripheral rim and positioned within the chamber, engaging the upstream end of the mat and indenting the mat through a portion of its longitudinal thickness in the areas of said ribs for causing the fibrous material to fluff out in the spaces between the ribs and thereby form regions of decreasing mat density progressively outward from said ribs,
    (d) a screen in the chamber disposed adjacent and upstream from the grill for trapping large particles of blood debris,
    (e) means for spacing the screen inwardly of the inlet port, forming therebetween an upstream recess for facilitating distribution of inflowing blood over the upstream surface of the mat, and
    (f) support means interposed between the downstream end of the mat and the outlet port for spacing the downstream end of the mat inwardly of the outlet port.

8. The blood filter of claim 7 including a pair of air outlet means, one communicating with the space between the screen and inlet port and the other with the space between the support means and outlet port for exhaustng blood-entrained air collected in said spaces.

* * * * *